(12) United States Patent
Park

(10) Patent No.: US 7,641,921 B1
(45) Date of Patent: Jan. 5, 2010

(54) ANTI-ANAL FISTULA COMPOSITION AND PROCESS FOR ITS MANUFACTURE

(76) Inventor: Chan Sik Park, 5266 O'Faly Rd., Fairfax, VA (US) 22030

(*) Notice: Subject to any disclaimer, the term of this patent is extended or adjusted under 35 U.S.C. 154(b) by 7 days.

(21) Appl. No.: 12/188,805

(22) Filed: Aug. 8, 2008

(51) Int. Cl.
*A01N 65/00* (2006.01)

(52) U.S. Cl. .................................................. 424/725

(58) Field of Classification Search ................. None
See application file for complete search history.

(56) References Cited

U.S. PATENT DOCUMENTS 6,916,494 B2  7/2005  Park

FOREIGN PATENT DOCUMENTS

| KR | 100173393 B1 | 10/1998 |
| KR | 1019990075992 A | 10/1999 |
| KR | 100364429 B1 | 11/2002 |

*Primary Examiner*—Michael V Meller
(74) *Attorney, Agent, or Firm*—Birch, Stewart, Kolasch & Birch, LLP

(57) ABSTRACT

The composition and process for preparing an anti-anal fistula composition which comprises providing a predetermined effective amount of natural substances of the genera Safflower, Notoginseng Radix, Lightyellow Sophora, Elecampane Redix, *Rumex*, Pine Resin, Sassafras Tree, Glycyrrhizae Radix, Testudinis Carapax, Rhei Rhizoma, Ephedrae Herba, Natrii Sulfas, Menthae Herba, Pasoniae Radix, Acontii Tuber, Corni Fructus, Gypsum, and Pelladendri Radix in an aqueous medium to form an initial mixture, extracting the initial mixture with water at a temperature of about 65°-75° C. for 1-2 hours to produce an aqueous mixture, filtering the aqueous mixture to produce a filtrate, and evaporating the filtrate to a moisture content of 30% to produce an extract which can be used as a treatment for hemorrhoid diseases including anal fistula.

10 Claims, No Drawings

ANTI-ANAL FISTULA COMPOSITION AND PROCESS FOR ITS MANUFACTURE

BACKGROUND OF THE INVENTION

1. Field of the Invention

The present invention relates to an anti-anal fistula composition made from natural substances and to a process for its manufacture. More particularly, the present invention is directed to a composition utilizing extracts of natural substances obtained from a combination of the genera Safflower, Notoginseng Radix, Lightyellow Sophora, Elecampane Redix, *Rumex*, Pine Resin, Sassafras Tree, Glycyrrhizae Radix, Testudinis Carapax, Rhei Rhizoma, Ephedrae Herba, Natrii Sulfas, Menthae Herba, Pasoniae Radix, Acontii Tuber, Corni Fructus, Gypsum, and Pelladendri Radix for use in treating anti-fistula patients, and to a process for its manufacture.

2. Description of Related Art

There are several types of known anti-hemorrhoid materials obtained from natural substances. For example, Korean Patent Publication No. 100173393 discloses an anti-hemorrhoid composition comprising Mugwort, Yin Yange Huo and Buckwheat flour in an amount of 10:10:1.5% by weight. The process comprises the steps of mixing together 10 g of Mugwort and 10 g of Yin Yange Huo, heating the initial mixture with 500 ml of water at a temperature of 100° C. for 30 minutes to produce 200 ml of an extract, and combining 200 ml of the extract with 1.5 g of Buckwheat and 1000 ml of salt water to finally producing a liquid extract which can be applied to the anus.

Korean Patent Publication No. 100364429 discloses anti-hemorrhoid composition comprising Salat Burnet Root, Wormwood, Horny Goat Weed and Chinese Matrimony Vine Root in the amount of about 30:30:20:20% by weight, respectively, and plus one or two selected from the group consisting of Korean Schisandra, Apricot Seed and Scholar Tree Flower in an amount of about 30% by weight.

The present inventor has U.S. Pat. No. 6,916,494 which discloses a composition and process for preparing an anti-hemorrhoid composition which comprises providing a predetermined effective amount of natural substances of the genera Glycyrrhizae Radix, Testudinis Carapax, Cervi Parvum Cornu, Rhei Rhizoma, Ephedrae Herba, Natrii Sulfas, Moutan Radicis Cortex, Menthae Herba, Pinelliae Rhizoma, Pasoniae Radix, Acontii Tuber, Corni Fructus, Gypsum, Ginseng Radix, Cinnabaris. Talcum and Pelladendri Radix in an aqueous medium to form an initial mixture, extracting the initial mixture with water at a temperature of about 70°-80° for 1-2 hours to produce an aqueous mixture, filtering the aqueous mixture to produce a filtrate, and evaporating the filtrate to a moisture content of 30% to produce an extract which can be used as a treatment for hemorrhoid diseases.

However, such conventional products and processes cannot be expected to fundamentally and effectively treat hemorrhoid disease. Also, such conventional products and processes are not effective in eliminating anal fistula in a short period of time.

It is unknown, however, to provide an anti-anal fistula composition made from the natural substances of the genera Safflower, Notoginseng Radix, Lightyellow Sophora, Elecampane Redix, *Rumex*, Pine Resin, Sassafras Tree, Glycyrrhizae Radix, Testudinis Carapax, Rhei Rhizoma, Ephedrae Herba, Natrii Sulfas, Menthae Herba, Pasoniae Radix, Acontii Tuber, Corni Fructus, Gypsum, and Pelladendri Radix in amounts of about 8.4:12.8:5.2:5.2:8.4:8.4:2.8:8.4:5.2:5.2:5.2:2.8:5.2:2.8:2.8:2.8:8.4:5.2% by weight, respectively.

Furthermore, none of the prior art processes disclose an anti-anal fistula extract which comprises extracts obtained from the above-identified natural substances. Accordingly, it is desirable to develop an improved composition and process for producing an anti-anal fistula composition for effectively treating anal fistula disease and effectively relieving the itch associated with hemorrhoidal diseases.

SUMMARY OF THE INVENTION

Accordingly, it is an object of the present invention to provide an anti-anal fistula composition obtained from natural substances and a process for its manufacture, which eliminates the above problems encountered with conventional anti-anal fistula compositions and methods of manufacture.

Another object of the present invention is to provide a composition utilizing an extract obtained from the genera Safflower, Notoginseng Radix, Lightyellow Sophora, Elecampane Redix, *Rumex*, Pine Resin, Sassafras Tree, Glycyrrhizae Radix, Testudinis Carapax, Rhei Rhizoma, Ephedrae Herba, Natrii Sulfas, Menthae Herba, Pasoniae Radix, Acontii Tuber, Corni Fructus, Gypsum, and Pelladendri Radix.

A further object of the present invention is to provide a process for manufacturing an anti-anal fistula extract from natural substances, such as Safflower, Notoginseng Radix, Lightyellow Sophora, Elecampane Redix, *Rumex*, Pine Resin, Sassafras Tree, Glycyrrhizae Radix, Testudinis Carapax, Rhei Rhizoma, Ephedrae Herba, Natrii Sulfas, Menthae Herba, Pasoniae Radix, Acontii Tuber, Corni Fructus, Gypsum, and Pelladendri Radix in amounts of about 8.4:12.8:5.2:5.2:8.4:8.4:2.8:8.4:5.2:5.2:5.2:2.8:5.2:2.8:2.8:2.8:8.4:5.2% by weight, respectively.

Still another object of the present invention is to provide a medical extract of natural substances for treating and/or providing relief for a patient who has anal fistula diseases and/or related itch diseases.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Referring now in detail to the present invention, there is provided with an anti-hemorrhoid composition for use as a medical extract, the composition being made from natural substances, namely Safflower (Peyote), Notoginseng Radix, Lightyellow Sophora, Elecampane Redix, *Rumex* Yellow Dock), Pine Resin, Sassafras (*Cinnamomum*) Tree, Glycyrrhizae Radix, Testudinis Carapax, Rhei Rhizoma, Ephedrae Herba, Natrii Sulfas, Menthae Herba, Pasoniae Radix, Acontii Tuber, Corni Fructus, Gypsum, and Pelladendri Radix Before the extraction, a portion of the natural substances, that is, Safflower, Notoginseng Radix, Lightyellow Sophora, Elecampane Redix, *Rumex*, Sassafras Tree, Glycyrrhizae Radix, Rhei Rhizoma, Ephedrae Herba, Menthae Herba, Pasoniae Radix, Acontii Tuber, Corni Fructus and Pelladendri Radix are preliminarily treated by washing with water to remove sand, clay, dust, and the like. After these substances are dried to a moisture content of about 5%, they are mixed together in a predetermined weight ratio and cut into a length of about 1 cm. After the preliminary treatment the balance of the natural substances listed above, that is, Testudinis Carapax, Natri Sulfas, Gypsum and Pine Resin are added to the mixture in a predetermined quantity.

In this time, the natural substances, Safflower, Notoginseng Radix, Lightyellow Sophora, Elecampane Redix, *Rumex*, Pine Resin, Sassafras, Glycyrrhizae Radix, Testudinis Carapax, Cervi Parvum Cornu, Rhei Rhizoma, Ephedrae Herba, Natrii Sulfas, Menthae Herba, Pasoniae Radix, Acontii Tuber, Corni Fructus, Gypsum, and Pelladendri Radix are present in an amount of about 7-9, about 11-14, about 4-6, about 4-6, about 7-9, about 7-9, about 2-4, about 7-9, about 4-6, about 4-6, about 4-6, about 2-4, about 4-6, about 2-4, about 2-4, about 2-4, about 7-9 and about 4-6% by weight, respectively, preferably in an amount of about 8.4:12.8:5.2:5.2:8.4:8.4:2.8:8.4:5.2:5.2:5.2:2.8:5.2:2.8:2.8:2.8:8.4:5.2% by weight, respectively.

The mixture is introduced to an extractor containing 6 times the volume of water as the mixture and soaked for about 1-2 hours at a temperature of about 65-75° C. The extracted mixture is first filtered through a centrifugal separator and then the filtrate is filtered again through a microfilter. At this time, the aromatic vapor collected in the extractor is recovered, condensed and reintroduced to the filtrate obtained from the initial mixture. The filtrate is evaporated by an automatic vacuum evaporator to a liquid content of about 30%. This concentrated liquid can be preferably administered in the form of a topical extract in order to treat or relieve hemorrhoidal disease. Also, the concentrated liquid can be dried in a dry sprayer to produce a powdered product. The powder can be formulated into a tablet form, pill form, suppository form, or ointment form, or the like in a conventional manner for use as an anti-anal fistula pharmaceutical product or a health food.

In as preferred aspect of the present process, about 10% by weight of both Glycyrrhizae Radix and Ginseng Radix, respectively, are preliminary heated at room temperature for about 2 hours and in a digester prior to being added to the mixture of natural substances, in order to further improve the anti-anal fistula effectiveness. It is preferred that the Ginseng Radix is produced in Korea.

In another embodiment of the present invention, about 1-2% by weight of other natural substances such as Puerariae Radix, Lycii Fructus, Platycodi Radix, Angelicae Gignantis Radix, *Poria Cocas* Wolf, Rehmanmiae Radix, Schizandrae Fructus, Paloniae Radix, Ponciri Fructus, Nepetae Spica, Astragali Radix, and Coptidis Rhizoma, respectively, can be added to the mixture in the extractor mentioned above, for further improving the anti-anal fistula effectiveness of the extract composition produced by the process of the present invention.

The natural substances used by the present invention have the following ingredients. Safflower (Peyote), contains mascaline, styrax oil, limolic acid and egonal. Notoginseng radix contains saponin, quercetin, β-sitosteral, and aucosteral. Lightyellow Sophora contains alkaloid, flavonoid, δ-matrine and δ-oxymatrine. Elecampane contains alatolactone, isolantolactone sequiterpene and alkaloids. *Rumex* (Yellow Dock) contains anthroquinone glycosides, oxalates and tannins. Pine Resin contains essential oil. Sassafras (Cinnamonium) Tree contains volatile oil, safrole, and 1-hydroxysafrole.

Glycyrrhizae Radix contains glycyrrhizin, liquiritigenin and liquiritin. Testudinis Carapax contains colloids, lipids and calcium salt. Rhei Rizoma contains emodin, chrysophanol and rhein. Ephedrae Herba contains ephedrine, pseudoephedrine and 1-norephedrine. Natrii Sulfas contains $N_{a2}SO_410H_2O$. Menthae Herba contains menthol, menthone and camphene. Paeoniae Radix contains paeoniflorin, oxypaloniflorin and tannin. Acontii Tuber contains aconitine, mesaconitine and hypaconitine. Corni Fructus contains marroniside, loganin and cornin. Gysum contains calcium sulfate and Pellodendii Radix contains beberin, obakunone and obakulactone.

The present invention also includes a method of treating hemorrhoid diseases such as anal fistula, external hemorrhoids, internal hemorrhoids, bloody stool, anus prolapsingo, skin rashes around the anal area, and the like by administering to the mammalian recipient about 0.05 g to 0.5 g/kg body weight per day, preferably 0.07 to 0.32/kg body weight per day of the dried composition thereof.

In order for the dried composition to have maximum effectiveness in treating anal fistula, the dried composition should be ingested orally about 4-6 times a day, preferably 3 times between meals. The composition in a tablet composition preferably contains 0.5 g to 1.5 g of dried composition, more preferably 1 g of the dried composition. When the composition is in the formulation of a powder, a pill, or an ointment, it will generally contain 1 g to 3 g of the dried composition. In order to use extract form, the extract contains a moisture content of about 30% for drink or tea.

The present invention will now be described in more detail in connection with the following examples which should be considered as being exemplary and not limiting the present invention.

EXAMPLE 1

Initially genera Safflower, Notoginseng Radix, Lightyellow Sophora, Elecampane Redix, *Rumex*, Sassafras Tree, Glycyrrhizae Radix, Rhei Rhizoma, Ephedrae Herba, Menthae Herba, Pasoniae Radix, Acontii Tuber, Corni Fructus, Gypsum, and Pelladendri Radix, respectively, are washed with water to remove sand, clay, dust and the like. These natural substances are cleaned and dried to a moisture content of approximately 5%.

68 g of Safflower, 256 g of Notoginseng Radix, 104 g of Lightyellow Sophora, 104 g of Elecampane Redix, 168 g of *Rumex*, 56 g of Sassafras Tree, 168 g of Glycyrrhizae Radix, 104 g of Rhei Rhizoma, 104 g of Ephedrae Herba, 104 g of Menthae Herba, 56 g of Pasoniae Radix, 56 g of Acontii Tuber, 56 g of Corni Fructus, and 104 g of Pelladendri Radix are cut into a particle size of about 1 cm and mixed together. To the mixture mentioned above are added, 104 g of Testidinis Carapax, 56 g of Natrii Sulfas, 168 g of Gypsum, and 168 g of Pine Resin. Thereafter, this mixture is placed in an extractor having an aromatic vapor collector. 12 l of water are added to approximately 2 Kg of the mixture in the extractor. The mixture in the extractor is heated up to about 75° C. for one hour and then extracted.

The aqueous mixture is filtered first in a centrifugal separator and then is filtered again in a microfilter. The aromatic vapor distilled from the aqueous mixture is condensed and added as an aromatic liquid to the filtrate. The filtrate is evaporated through an automatic vacuum evaporator to a moisture content of about 30% to produce an extract which is useful as an anti-anal fistula composition in extract form. At this time, the concentrated liquid is dried through a dry sprayer to produce a granulated formulation, a table formulation, a pill formulation, an ointment formulation, or the like, for use as an anti-anal fistula medicine drink or tea.

EXAMPLE 2

The natural substances are cleaned and cut as the above Example 1. First of all, 200 g of Glycyrrhizae Radix and 200 g of Ginseng Radix produced in Korea, are preliminarily heated at a temperature of 25° C., and in a digester containing 6 times the volume of water for 2 hours. The mixture of Glycyrrhizae Radix, Ginseng Radix and liquid in the digester is moved to an extractor. After then, to this mixture in the extractor, 168 g of Safflower, 104 g of Lightyellow Sophora, 104 g of *Rumex*, 104 g of Rhei Rhizoma, 104 g of Ephedrae Herba, 104 g of Menthae Herba, 56 g of Pasoniae Radix, 56 g of Acontii Tuber, 56 g of Corni Fructus, 168 g of Notoginseng Radix, 104 g of Pelladendri Radix, 104 g of Testudinis Carapax, 56 g of Natrii Sulfas, 168 g of Gypsum, 56 g of Sassafras Tree, and 168 g of Pine Resin are added. Thereafter, the procedure of Example 1 is repeated to produce an anti-anal fistula composition and tea for use in treating and relieving hemorrhoid disease.

Test Example 1

Treatment of Anal Fistula

Won S. Lee is a 61-year-old man weighing 72 kg was diagnosed as having chronic anal fistula, having suffered with this disease for more than eleven years. The symptoms accompanied with stomach pain were especially noticeable after drinking alcoholic beverages or ingesting spicy food. Also, the sciatica of hip bone was a serious one. Therefore, he could not drive his car. He was given a sixty-day Kyunghee Herb's (inventor's clinic) extract treatment in two consecutive periods, with an interval of fifteen days between them. During the first half of the procedure, four tablets were given each day, each between the meals. It was noted that the anal fistula, bloody stool, stomach pain and hip bone pain were considerably reduced after the first half of the procedure. After sixty days, the anal fistula, bloody stool, stomach pain and hip bone pain disappeared.

Test Example 2

Treatment of Prolapsing of Anus

Il J. Kim is a 42-year-old woman weighing 51 kg, who was diagnosed with severe hemorrhoids along with prolapsing of the anus for eight years. After he tried the Kyunghee Herb's extract for one month, she experienced relief and after drinking the extract for four months more, he was completely healed of the prolapsing of anus.

Test Example 3

Treatment of Bloody Stool

Suk J. Lee is a 55-year-old man, weighing 70 kg was diagnosed as having chronic bloody stool, having suffered with this disease for about seven years. The symptoms accompanied with severe abdominal pain were noticeable. He was given two-month Kyunghee Herb's oriental tea treatment, and he was cured of stomach pain and bloody stool within two months.

Test Example 4

Treatment of Anal Fistula

Myong J. Park is a 37-year-old woman, weighing 53 kg, who has had severe anal fistula, especially, when she was in her menses. After she took Kyunghee Herb's tablets and herbal tea for three months, she had completely cured her anal fistula.

Test Example 5

Treatment of Anal Fistula

Jung H. Park is a 31-year-old woman, weighing 50 kg, who has had chronical anal fistula for five years. After she was given Kyunghee Herb's herbal tea for three months, she was cured of anal fistula.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A composition comprising a pharmaceutically effective amount of extracts of Safflower, Notoginseng Radix, Lightyellow Sophora, Elecampane Redix, *Rumex*, Pine Resin, Sassafras Tree, Glycyrrhizae Radix, Testudinis Carapax, Rhei Rhizoma, Ephedrae Herba, Natrii Sulfas, Menthae Herba, Pasoniae Radix, Acontii Tuber, Corni Fructus, Gypsum, and Pelladendri Radix.

2. The composition of claim 1, wherein

Safflower is present in an amount of about 7-9 by weight,
Notoginseng Radix is present in an amount of about 11-4% by weight,
Lightyellow Sophora is present in an amount of about 4-6% by weight,
Elecampane Redix is present in an amount of about 4-6% by weight,
*Rumex* is present in an amount of about 7-9% by weight,
Pine Resin is present in an amount of about 7-9% by weight,
Sassafras Tree is present in an amount of about 2-4% by weight,
Glycyrrhizae Radix is present in an amount of about 7-9% by weight,
Testudinis Carapax is present in an amount of about 4-6% by weight,
Rhei Rhizoma is present in an amount of about 4-6% by weight,
Ephedrae Herba is present in an amount of about 4-6% by weight,
Natrii Sulfas is present in an amount of about 4-6% by weight,
Moutan Radicis Cortex is present in an amount of about 2-4% by weight,
Menthae Herba is present in an amount of about 7-9% by weight,
Pasoniae Radix is present in an amount of about 7-9% by weight,
Acontii Tuber is present in an amount of about 2-4% by weight, Corni Fructus is present in an amount of about 2-4% by weight,
Gypsum is present in an amount of about 7-9% by weight, and
Pelladendri Radix is present in an amount of about 4-6% by weight.

3. The composition of claim 1, wherein
Safflower is present in an amount of about 8.4% by weight,
Notoginseng Radix is present in an amount of about 12.8% by weight,
Lightyellow Sophora is present in an amount of about 5.2% by weight,
Elecampane Redix is present in an amount of about 5.2% by weight,
*Rumex* is present in an amount of about 8.4% by weight,
Pine Resin is present in an amount of about 8.4% by weight,
Sassafras Tree is present in an amount of about 2.8% by weight,
Glycyrrhizae Radix is present in an amount of about 8.4% by weight,
Testudinis Carapax is present in an amount of about 5.2% by weight,
Rhei Rhizoma is present in an amount of about 5.2% by weight,
Ephedrae Herba is present in an amount of about 5.2% by weight,
Natrii Sulfas is present in an amount of about 2.8% by weight,
Menthae Herba is present in an amount of about 5.2% by weight,
Pasoniae Radix is present in an amount of about 2.8% by weight,
Acontii Tuber is present in an amount of about 2.8% by weight,
Corni Fructus is present in an amount of about 2.8% by weight,
Gypsum is present in an amount of about 8.4% by weight, and
Pelladendri Radix is present in an amount of about 5.2% by weight.

4. The composition of claim 1, wherein
Safflower is present in an amount of about 8.4% by weight,
Notoginseng Radix is present in an amount of about 1.2% by weight,
Lightyellow Sophora is present in an amount of about 5.2% by weight,
Elecampane Redix is present in an amount of about 5.2% by weight,
*Rumex* is present in an amount of about 8.4% by weight,
Pine Resin is present in an amount of about 8.4% by weight,
Sassafras Tree is present in an amount of about 2.8% by weight,
Glycyrrhizae Radix is present in an amount of about 10% by weight,
Ginseng Radix is present in an amount of about 10% by weight,
Testudinis Carapax is present in an amount of about 5.2% by weight,
Rhei Rhizoma is present in an amount of about 5.2% by weight,
Ephedrae Herba is present in an amount of about 5.2% by weight,
Natrii Sulfas is present in an amount of about 2.8% by weight,
Menthae Herba is present in an amount of about 5.2% by weight,
Pasoniae Radix is present in an amount of about 2.8% by weight,
Acontii Tuber is present in an amount of about 2.8% by weight,
Corni Fructus is present in an amount of about 2.8% by weight,
Gypsum is present in an amount of about 8.4% by weight, and
Pelladendri Radix is present in an amount of about 5.2% by weight.

5. A process for preparing
(a) mixing together a pharmaceutically effective amount of the extracts of claim 1 in an aqueous media to form an initial mixture,
(b) extracting said initial mixture with water at a temperature of about 65'-75° C. for about 1-2 hours to produce an aqueous mixture,
(c) filtrating said aqueous mixture to produce a filtrate, and
(d) evaporating said filtrate down to a moisture content of about 30% to produce a medicinal extract.

6. The process of claim 5, wherein the extracts of Safflower, Notoginseng Radix, Lightyellow Sophora, Elecampane Redix, *Rumex*, Pine Resin, Sassafras Tree, Glycyrrhizae Radix, Testudinis Carapax, Rhei Rhizoma, Ephedrae Herba, Natrii Sulfas, Menthae Herba, Pasoniae Radix, Acontii Tuber, Corni Fructus, Gypsum, and Pelladendri Radix are used in an amount of about 7-9%, about 11-14%, about 4-6%, about 4-6%, about 7-9%, about 2-4%, about 7-9%, about 4-6%, about 4-6%, about 4-6%, about 2-4%, about 2-4%, about 7-9%, and about 4-6% by weight, respectively.

7. The process of claim 6, wherein the extracts of Safflower, Notoginseng Radix, Lightyellow Sophora, Elecampane Redix, *Rumex*, Pine Resin, Sassafras Tree, Glycyrrhizae Radix, Testudinis Carapax, Rhei Rhizoma, Ephedrae Herba, Natrii Sulfas, Menthae Herba, Pasoniae Radix, Acontii Tuber, Corni Fructus, Gypsum, and Pelladendri Radix are used in amounts of about 8.4%, about 12.8%, about 5.2%, about 5.2%, about 8.4%, about 8.4%, about 2.8%, about 8.4%, about 5.2%, about 5.2%, about 2.8%, about 5.2%, about 2.8%, about 2.8%, about 2.8%, about 8.4% and about 5.2% by weight, respectively.

8. The process of claim 5, wherein the extracts of Glycyrrhizae Radix and Ginseng Radix are preliminarily heated in a digester at a room temperature for about 2 hours prior to being mixed with the other extracts.

9. The process of claim 5, wherein the extracting is conducted at a temperature of about 75° C. for about one hour.

10. The anti-fistula composition comprising an extract produced by the process of claim 5.

* * * * *